US007627370B2

(12) United States Patent
Marks

(10) Patent No.: US 7,627,370 B2
(45) Date of Patent: Dec. 1, 2009

(54) BRAIN FUNCTION DECODING PROCESS AND SYSTEM

(76) Inventor: Donald H. Marks, 1133 Lakeridge Dr., Hoover, AL (US) 35244

( * ) Notice: Subject to any disclaimer, the term of this patent is extended or adjusted under 35 U.S.C. 154(b) by 721 days.

(21) Appl. No.: 11/180,871

(22) Filed: Jul. 13, 2005

(65) Prior Publication Data

US 2006/0084858 A1  Apr. 20, 2006

Related U.S. Application Data

(60) Provisional application No. 60/620,507, filed on Oct. 20, 2004, provisional application No. 60/637,268, filed on Dec. 17, 2004.

(51) Int. Cl.
*A61B 5/0476* (2006.01)
*A61B 5/05* (2006.01)

(52) U.S. Cl. .......................... 600/544; 600/407

(58) Field of Classification Search .............. 600/407, 600/410, 544; 424/9.2–9.5; 382/274–294, 382/309
See application file for complete search history.

(56) References Cited

U.S. PATENT DOCUMENTS

| | | | | |
|---|---|---|---|---|
| 5,370,126 | A | * | 12/1994 | Clifford, Jr. ................ 600/544 |
| 5,664,077 | A | * | 9/1997 | Kubo ......................... 345/421 |
| 6,462,736 | B1 | * | 10/2002 | Ross et al. .................. 345/419 |
| 2002/0058867 | A1 | * | 5/2002 | Breiter et al. ............... 600/407 |
| 2002/0062089 | A1 | * | 5/2002 | Johnson, Jr. ................ 600/544 |
| 2002/0103429 | A1 | * | 8/2002 | deCharms ................... 600/410 |
| 2005/0154290 | A1 | * | 7/2005 | Langleben .................. 600/410 |

OTHER PUBLICATIONS

Beauchamp et al. Dynamic functional changes associated with cognitive skill learning of an adapted version of the Tower of London task. NeuroImage (2003) 20:1649-1660.
Bernard et al. The hippocampal region is involved in successful recognition of both remote and recent famous faces. NeuroImage (2004) 22:1704-1714.
Binder et al. Conceptual Processing during the Conscious Resting State: A Functional MRI Study. J Cogn Neurosci (1999) 11(1):80-93.
Binder et al. Neural Correlates of Lexical Access during Visual Word Recognition. J Cogn Neurosci (2003) 15(3):372-393.
Binkofski et al. Supramodal Representation of Objects and Actions in the Human Inferior Temporal and Ventral Premotor Cortex. Cortex (2004) 40:159-161.

(Continued)

*Primary Examiner*—Eric F Winakur
*Assistant Examiner*—Lawrence N Laryea
(74) *Attorney, Agent, or Firm*—Gifford, Krass, Sprinkle, Anderson & Citkowski, P.C.

(57) ABSTRACT

A method of interpreting cognitive response to a stimulus is disclosed. The method includes collecting baseline neural activity data from a subject absent a stimulus. Neural activity data is collected while the subject is being stimulated through exposure to a stimulus. A unique three-dimensional cognitive engram is then plotted representative of cerebral regions of stimulated neural activity caused by the stimulus. A novel graphical representation is plotted in three dimensions to indicate the brain region response unique to that stimulus.

21 Claims, 6 Drawing Sheets
(5 of 6 Drawing Sheet(s) Filed in Color)

OTHER PUBLICATIONS

Blonder et al. Regional brain response to faces of humans and dogs. Cogn Brain Res (2004) 20:384-394.

Bloom et al. Determination of Drug-Induced Changes in Functional MRI Signal Using a Pharmacokinetic Model. Hum Brain Mapp (1999) 8:235-244.

Bodurka et al. Toward Direct Mapping of Neuronal Activity: MRI Detection of Ultraweak, Transient Magnetic Field Changes. Magn Reson Med (2002) 47:1052-1058.

Brass et al. Selection for Cognitive Control: A Functional Magnetic Resonance Imaging Study on the Selection of Task-Relevant Information. J Neurosci (2004) 24(40):8847-8852.

Buhmann et al. Pharmacologically modulated fMRI-cortical responsiveness to levodopa in drug-naive hemiparkinsonian patients. Brain (2003) 126:451-461.

Cabeza et al. Imaging Cognition II: An Empirical Review of 275 PET and fMRI Studies. J Cogn Neurosci (2000) 12(1):1-47.

Canli et al. Brain activation to emotional words in depressed vs healthy subjects. NeuroReport (2004) 15(17):2585-2588.

Chao et al. Attribute-based neural substrates in temporal cortex for perceiving and knowing about objects. Nat Neurosci (1999) 2(10):913-919.

Chua et al. A Functional Anatomy of Anticipatory Anxiety. NeuroImage (1999) 9:563-571.

Courtney et al. The role of prefrontal cortex in working memory: examining the contents of consciousness. Phil Trans R Soc Lond B (1998) 353:1819-1828.

Deco et al. "What" and "Where" in Visual Working Memory: A Computational Neurodynamical Perspective for Integrating fMRI . . . J Cogn Neurosci (2004) 16(4):683-701.

Fiebach et al. Processing concrete words: fMRI evidence against a specific right-hemisphere involvement. Neuropsychologia (2003) 42:62-70.

Fletcher et al. Frontal lobes and human memory-Insights from functional neuroimaging. Brain (2001) 124:849-881.

Fossati et al. Neuroplasticity: from MRI to depressive symptoms. Eur Neuropsychopharmacol (2004) 14:S503-S510.

Fu et al. Attenuation of the Neural Response to Sad Faces in Major Depression by Antidepressant Treatment. Arch Gen Psychiatry (2004) 61:877-889.

Fujii et al. Encoding-related brain activity during deep processing of verbal materials: a PET study. Neurosci Res (2002) 44:429-438.

Gaillard et al. Functional anatomy of cognitive development-fMRI of verbal fluency in children and adults. Neurology (2000) 54:180-185.

Gaillard et al. Development Aspects of Language Processing: fMRI of Verbal Fluency in Children and Adults. Hum Brain Mapp (2003) 18:176-185.

Gevins et al. Electroencephalographic imaging of higher brain function. Phil Trans R Soc Lond B (1999) 354:1125-1134.

Gonsalves et al. Neural Evidence That Vivid Imagining Can Lead to False Remembering. Psychol Sci (2004) 15(10):655-660.

Gross et al. Properties of MEG tomographic maps obtained with spatial filtering. NeuroImage (2003) 19:1329-1336.

Hagoort. How the brain solves the binding problem for language: a neurocomputational model of syntactic processing. NeuroImage (2003) 20:S18-S29.

Haller et al. Hippocampal MR Imaging Morphometry by Means of General Pattern Matching. Radiology (1996) 199:787-791.

Hartley et al. Locating and Fractionating Working Memory Using Functional Neuroimaging: Storage, Maintenance, and Executive Functions. Microsc Res Tech (2000) 51:45-53.

Haxby et al. Distributed and Overlapping Representations of Faces and Objects in Ventral Temporal Cortex. Science (2001) 293:2425-2430.

Hayes et al. An fMRI Study of Episodic Memory: Retrieval of Object, Spatial, and Temporal Information. Behav Neurosci (2004) 118(5):885-896.

Ishai et al. Distributed representation of objects in the human ventral visual pathway. Proc Natl Acad Sci USA (1999) 96:9379-9384.

Ishai et al. The Representation of Objects in the Human Occipital and Temporal Cortex. J Cogn Neurosci (2000) 12(2):35-51.

Ishai et al. Visual Imagery of Famous Faces: Effects of Memory and Attention Revealed by fMRI. NeuroImage (2002) 17:1729-1741.

Ishai et al. Repetition suppression of faces is modulated by emotion. PNAS (2004) 101(26):9827-9832.

Juengling et al. Prefrontal cortical hypometabolism during low-dose interferon alpha treatment. Psychopharmacology (2000) 152:383-389.

Kim et al. In vivo mapping of functional domains and axonal connectivity in cat visual cortex using magnetic resonance imaging. Magn Reson Imaging (2003) 21:1131-1140.

Kircher et al. Towards a functional neuroanatomy of self processing: effects of faces and words. Cogn Brain Res (2000) 10:133-144.

Knight et al. Neural Substrates Mediating Human Delay and Trace Fear Conditioning. J Neurosci (2004) 24(1):218-228.

Koechlin et al. The Architecture of Cognitive Control in the Human Prefrontal Cortex. Science (2003) 302:1181-1185.

Kozel et al. A Pilot Study of Functional Magnetic Resonance Imaging Brain Correlates of Deception in Healthy Young Men. J Neuropsychiatry Clin Neurosci (2004) 16(3):295-305.

Kozel et al. A Replication Study of the Neural Correlates of Deception. Behav Neurosci (2004) 118(4):852-856.

Lange. What can modern statistics offer imaging neuroscience? Stat Methods Med Res (2003) 12:447-469.

Langleben et al. Brain Activity during Simulated Deception: An Event-Related Functional Magnetic Resonance Study. NeuroImage (2002) 15:727-732.

Lanius et al. The Nature of Traumatic Memories: A 4-T fMRI Functional Connectivity Analysis. Am J Psychiatry (2004) 161(1):1-9.

Lee et al. Lie Detection by Functional Magnetic Resonance Imaging. Hum Brain Mapp (2002) 15:157-164.

Makris et al. MRI-based surface-assisted parcellation of human cerebellar cortex: An anatomically specified method with estimate of reliability. NeuroImage (2005) 25:1146-1160.

Marshall et al. Cerebral localization, then and now. NeuroImage (2003) 20:S2-S7.

Matthews et al. Functional magnetic resonance imaging. J Neural Neurosurg Psychiatry (2004) 75:6-12.

Matthews et al. Contribution of Functional Neuroimaging to Understanding Neuropsychiatric Side Effects of Interferon in Hepatitis C. Psychosomatics (2004) 45(4):281-286.

McGonigle et al. Variability in fMRI: An Examination of Intersession Differences. NeuroImage (2000) 11:708-734.

Mechelli. Commentary on "Functional MRI and the Study of Human Consciousness" by Daniel Lloyd. J Cogn Neurosci (2002) 14(6):834-835.

Mukamel et al. Coupling Between Neuronal Firing, Field Potentials, and fMRI in Human Auditory Cortex. Science (2005) 309:951-954.

Mungas et al. MRI predictors of cognition in subcortical ischemic vascular disease and Alzheimer's disease. Neurology (2001) 57:2229-2235.

Na et al. Functional MR Imaging of Working Memory in the Human Brain. Korean J Radiol (2000) 1(1):19-24.

Nielsen et al. Mining for associations between text and brain activation in a functional neuroimaging database. (2005).

Ogawa et al. Brain magnetic resonance imaging with contrast dependent on blood oxygenation. Proc Natl Acad Sci USA (1990) 87:9868-9872.

Okado et al. Neural processing associated with true and false memory retrieval. Cogn Affect Behav Neurosci (2003) 3(4):323-334.

Olesen et al. Increased prefrontal and parietal activity after training of working memory. Nat Neurosci (2004) 7(1):75-79.

Pietrini et al. Beyond sensory images: Object-based representation in the human ventral pathway. PNAS (2004) 101(15):5658-5663.

Prabhakaran et al. Integration of diverse information in working memory within the frontal lobe. Nat Neurosci (2000) 3(1):85-90.

Ritter. Brain Cells 'Recognize' Famous People. Yahoo! News (2005).

Robertson. Memory and the Brain. J Dent Educ (2002) 66(1):30-42.

Rugg et al. The neural basis of episodic memory: evidence from functional neuroimaging. Phil Trans R Soc Lond B (2002) 357:1097-1110.

Shallice. Functional imaging and neuropsychology findings: how can they be linked? NeuroImage (2003) 20:S146-S154.

Smith et al. Altered brain activation in cognitively intact individuals at high risk for Alzheimer's disease. Neurology (1999) 53:1391-1396.

Stuss et al. The frontal lobes are necessary for 'theory of mind'. Brain (2001) 124:279-286.

Suppes et al. Brain-wave recognition of sentences. Proc Natl Acad Sci USA (1998) 95:15861-15866.

Thomas. Assessing Brain Development Using Neurophysiologic and Behavioral Measures. J Pediatr (2003) 143:S46-S53.

Vogel et al. Neural activity predicts individual differences in visual working memory capacity. Nature (2004) 428:748-751.

Vythilingham et al. Hippocampal Volume, Memory, and Cortisol Status in Major Depressive Disorder: Effects of Treatment. Biol Psychiatry (2004) 56:101-112.

Wagner et al. When encoding yields remembering: insights from event-related neuroimaging. Phil Trans R Soc Lond B (1999) 354:1307-1324.

Wood et al. Hippocampal Neurons Encode Information about Different Types of Memory Episodes Occurring in the Same Location. Neuron (2000) 27:623-633.

* cited by examiner

BRAIN FUNCTION DECODING PROCESS AND SYSTEM

RELATED APPLICATION

This application claims priority of U.S. Provisional Patent Application Ser. No. 60/620,507 filed Oct. 20, 2004, and U.S. Provisional Patent Application Ser. No. 60/637,268 filed Dec. 17, 2004, which are incorporated herein by reference.

FIELD OF THE INVENTION

The present invention in general relates to analysis of neuroimaging data and in particular to identification of an individual's response to a sensory or physiologic stimulation through analysis of neuroimaging data.

BACKGROUND OF THE INVENTION

Scientific research has demonstrated that memory and consciousness reside in the organization of neurons, their interconnections, charges on the cell surfaces, intracellular and extracellular proteins and other molecules, and other factors. Although the ability to understand the molecular and cellular mechanism of memory and consciousness, the sequences, the charges, and how they relate to memory and consciousness is in very early development, the capability to record and analyze these data in detail exists now.

Great strides have been made in the area of functional and structural imaging of the human brain. The ability to interpret and correlate brain imaging information and the stimuli that result in memories, thoughts and concepts is ready for development. The technology for imaging the macroscopic, microscopic and molecular structure of individual human brains, through techniques such as Computed Axial Tomography (CT or CAT), functional Magnetic Resonance Imaging (fMRI), Positron Emission Tomography (PET), electroencephalography (EEG), and Magnetoencephalography (MEG) (collectively referred hereafter as neuroimaging technologies) is continually improving. Recent progress in improved imaging resolution and advancing computational analysis of the data has led to evolving understanding of where thoughts are encoded in the brain.

Neuroanatomy Using Imaging

Kim et al. (2003) used Blood Oxygenation Level-Dependent (BOLD)-based functional MRI (fMRI) and diffusion tensor imaging (DTI) on the cat visual cortex to allow three-dimensional fiber reconstruction, to construct a map of the axonal circuitry underlying visual information processing. Rueckert et al. (2003) used the concept of statistical deformation modeling to construct average models of neuroanatomy and variability of 25 different human subjects. With newer MRI machines with stronger (3 Tesla and above) magnetic fields and improved software, cellular resolution is now being attempted.

Brain Organization and Imaging

Zeineh et al. (2003) used high-resolution FMRI to study the process of encoding and retrieval of memories of names associated with faces, in the medial temporal lobe (MTL) of the human brain and its subregions. The cornu ammonis and the dentate gyrus regions of the brain were active relative to baseline only during encoding, and this activity decreased as associations were learned. Activity in the subiculum region showed the same temporal decline, but primarily during retrieval. Zeineh and colleagues evaluated changes in the blood oxygen level-dependent (BOLD) response, reflecting neural activity, within different substructures of the MTL, as subjects progressively learned new associations. These researchers developed techniques to acquire high-resolution structural (0.4 by 0.4 mm) and functional (1.6 by 1.6 mm) MRI data and to localize functional activity precisely within the substructures of the hippocampus. Similar work, with modifications in technique, particularly stimulus and matching activity, forms one of the basic techniques of patent application #10218 for cognitive engineering. Zieneh et al. manipulated the imaging data to mathematically represent an "unfolding" of the hippocampal cortex, which revealed the entirety of each hippocampal subregion (within the resolution restrictions of the equipment) and adjacent neocortical regions (parahippocampal, entorhinal, perirhinal, and fusiform) in a single plane, or "flat map" representation. Boundaries were demarcated between the architectonic subregions on the high-resolution structural MR images. The white matter and CSF throughout the MTL were segmented and separated out, retaining only the gray matter sheath. Gray matter was then computationally extracted and flattened (similar to flattening the globe into a flat map of the world) to project the demarcated boundaries to produce unfolded flattened maps of the hippocampus.

Using these techniques, Zeineh et al. studied ten subjects, who were scanned while they performed a face-name association task in which a series of unfamiliar (could be familiar) faces were paired with names. Computational warping techniques transformed an individual subject's hippocampal maps to the flat hippocampal template space. The same transformation parameters were then applied to the coregistered functional MRI scans, which delivered high-resolution fMRI data in a standardized flat space. This procedure enabled measuring activity over time in each subregion and to perform powerful group statistics across subjects. Similarly, cognitive engineering will create a data model of a concept, and of specific visual objects, such as a face.

Zeineh and colleagues were able to show a strong, parametric correlation between activity in specific brain areas and the storage of new associations. As the number of new associations learned decreased from block to block, activity in these regions fell in parallel. They also found a similarly strong relationship between activity in the subiculum and retrieval of newly learned associations.

Because subjects vary in the anatomy of their MTLs, Zeineh et al. constructed a template representing the typical anatomy of the subject population by averaging together the individual demarcation boundaries across subjects. This is somewhat analogous to the work of Rueckert (automatic construction of three-dimensional statistical deformation models (SDM) of the brain using nonrigid registration). Using a group-averaged incremental performance curve, the researchers regressed MR signal intensity in each pixel and each subject with two waveforms reflecting either performance during learning or performance during retrieval, and then statistically tested whether the slope of each regression for a given pixel was on average different from zero.

In summary, Zeineh et al. identified mnemonic properties of different subregions within the hippocampal circuitry as human subjects learned to associate names with faces. The cornu ammonis (CA) .elds 2 and 3 and the dentate gyrus were active relative to baseline only during encoding, and this activity decreased as associations were learned. Activity in the subiculum showed the same temporal decline, but primarily during retrieval.

Ishai and Ungerleider (1999) identified, using FMRI, three bilateral regions in the ventral temporal cortex that responded preferentially to faces, houses, and chairs. In a follow-up report (Ishai 2000) they demonstrated differential patterns of activation, similar to those seen in the ventral temporal cortex, in the bilateral regions of the ventral occipital cortex. They also found category-related responses in the dorsal occipital cortex and in the superior temporal sulcus. Moreover, rather than activating discrete, segregated areas, each category was associated with its own differential pattern of response across a broad expanse of cortex.

The distributed patterns of response were similar across tasks (passive viewing, delayed matching) and presentation formats (photographs, line drawings). Ishai et al. (2000) proposed that the representation of objects in the ventral visual pathway, including both occipital and temporal regions, is not restricted to small, highly selective patches of cortex but, instead, is a distributed representation of information about object form. Within this distributed system, the representation of faces appears to be less extensive as compared to the representations of non-face objects.

Koechlin et al. (2003) showed that the lateral pre-frontal cortex (PFC) of the brain is organized as a cascade of executive (controlling) processes from premotor to anterior PFC regions. These processes control behavior according to stimuli, the present perceptual context, and the temporal episode in which stimuli occur, respectively. Koechlin et al.'s results support a unified modular model of cognitive control that describes the overall functional organization of the human lateral PFC and has basic methodological and theoretical implications.

Fan et al. (2003) studied whether source information, item information, or both are required at the time of memory retrieval. Two sources were used in a factorial design in which the main effect of source and item retrieval, along with their interaction, could be measured by fMRI activations. They found that when source information was required at retrieval, the left frontal lobe showed significant activation but not when item retrieval was required. Activation of the hippocampal section of the brain showed no difference between source and item retrieval. Fan et al.'s data supports a larger role for the frontal lobes in encoding and retrieval of source information.

Nielson et al. (2004), utilizing statistical data mining of a neuroimaging database, located associations between various words/text and brain locations. This provided an understanding of how the brain associates words indicative of cognitive function.

It appears that in all of the studies to date, neuroimaging researchers have mapped gross brain functional activation with various macroscopic regions of the brain. There has not been an attempt to understand how individual brain imaging is directly linked to the concepts that form the basis of thought. This is the principal area in which the present (Cognitive Engineering® 10218) patent application differs.

Correlations Between Functioning of Various Brain Regions

Givens et al. (1999) reviewed their and other data using EEG to study higher brain function. They emphasized the ability of more modern EEG studies to complement functional neuroimaging techniques. The current invention (Cognitive Engineering® 10218) may utilize multiple simultaneous neuroimaging techniques, including supplementation by EEG, during the construction of some data sets.

Suppes et al. (1998) studied the ability of recordings of electrical and magnetic brain waves of two subjects to recognize which one of twelve sentences or seven words auditorily presented was processed. The analysis consisted of averaging over trials to create prototypes and test samples, to each of which a Fourier transform was applied, followed by filtering and an inverse transformation to the time domain. The filters used were optimal predictive filters, selected for each subject. A still further improvement was obtained by taking differences between recordings of two electrodes to obtain bipolar pairs that then were used for the same analysis. Recognition rates, based on a least-squares criterion, varied, but the best were above 90%. The first words of prototypes of sentences also were cut and pasted to test, at least partially, the invariance of a word's brain wave in different sentence contexts. The best result was above 80% correct recognition. Test samples made up only of individual trials also were analyzed. The best result was 134 correct of 288 (47%), compared to the expected recognition number by chance (24, or 8.3%).

Hartley and Speer (2000) reviewed functional neuroimaging data of memory, and discussed progress in understanding memory systems. Rugg et al. (2002) reviewed FMRI use to study episodic memory in humans. The data they review, while impressive, does not localize below general brain region areas of activation.

Fujii et al. (2002) used PET to image normal volunteers engaged in deep (semantic) or shallow (phonological) processing of new or repeated words. Their results showed that deep processing, compared with shallow processing, resulted in significantly better recognition performance and that this effect was associated with activation of various brain areas. Regions directly relevant to episodic memory encoding were located in the anterior part of the parahippocampal gyrus, inferior frontal gyrus, supramarginal gyrus, anterior cingulate gyrus, and medial frontal lobe in the left hemisphere. The authors concluded that several regions, including the medial temporal lobe, play a role in episodic memory encoding.

Zhang et al. (2003) studied the involvement of frontal cortex in accessing and evaluating information in working memory using a variant of a Sternberg paradigm and comparing brain activations between positive and negative responses (known to differentially tax access/evaluation processes). Test subjects remembered two trigrams in each trial and were then cued to discard one of them and maintain the other one as the target set. After a delay, a probe letter was presented and participants made decisions about whether or not it was in the target set. Several frontal areas—anterior cingulate (BA32), middle frontal gyrus (bilateral BA9, right BA10, and right BA46), and left inferior frontal gyrus (BA44/45)—showed increased activity when participants made correct negative responses relative to when they made correct positive responses. No areas activated significantly more for the positive responses than for the negative responses. The authors suggested that the multiple frontal areas involved in the test phase of this task may reflect several component processes that underlie more general frontal functions.

Schmithorst and Holland (2004) used fMRI to study neural correlates of the link between formal musical training and mathematics performance in normal adults. Musical training was associated with increased activation in the left fusiform gyrus and prefrontal cortex areas of the brain, and decreased activation in visual association areas and the left inferior parietal lobule of the brain during a mathematical task. The authors hypothesized that the correlation between musical training and math proficiency may be associated with improved working memory performance and an increased abstract representation of numerical quantities.

Lanius et al. (2004) used both 4-T fMRI and functional connectivity analyses to assess interregional brain activity correlations during the recall of traumatic memories in traumatized subjects with and without posttraumatic stress disorder (PTSD). Comparison of connectivity maps at the right anterior cingulate gyrus brain region for the two groups showed that the subjects without PTSD had greater correlation than the PTSD subjects in the following brain areas: left superior frontal gyrus (Brodmann's area 9), left anterior cingulate gyrus (Brodmann's area 32), left striatum (caudate), left parietal lobe (Brodmann's areas 40 and 43), and left insula (Brodmann's area 13). In contrast, the PTSD subjects showed greater correlation than the subjects without PTSD in the right posterior cingulate gyrus (Brodmann's area 29), right caudate, right parietal lobe (Brodmann's areas 7 and 40), and right occipital lobe (Brodmann's area 19). The authors concluded that the differences in brain connectivity between PTSD and comparison subjects may account for the nonverbal nature of traumatic memory recall in PTSD subjects, compared to a more verbal pattern of traumatic memory recall in comparison subjects.

Visual Recognition in the Brain

Na et al. (2000) used fMRI to image working memory in humans. Like all studies to date, they were able to determine gross brain areas of activation, but were limited on their resolution. Na et al. assessed activated brain areas during stimulation tasks (item recognition), followed by an activation period. The prefrontal cortex and secondary visual cortex were activated bilaterally by both verbal and visual working memory tasks, and the patterns of activated signals were similar in both tasks. Bilateral prefrontal and superior parietal cortices activated by the visual working memory task may be related to the visual maintenance of objects, representing visual working memory.

Their activation map images of the upper level of the brain showed neither activated signals in the supramarginal gyrus nor lateralization of activated signals in the frontal and parietal lobes. Map image of the middle level of the brain showed no activated signals in the left inferior frontal or temporal gyrus. An activated signal in the prefrontal cortex corresponded to the signal activated during the verbal working memory task. Map image of the lower level of the brain showed bilateral activated signals similar to those seen during the verbal working memory task in the right and left occipital cortices and posterior fusiform gyri.

Zhang et al. (2003) compared brain activations between positive and negative responses (known to differentially tax access/evaluation processes) to investigate the involvement of frontal cortex in accessing and evaluating information in working memory. Participants remembered two trigrams in each trial and were then cued to discard one of them and maintain the other one as the target set. After a delay, a probe letter was presented and participants made decisions about whether or not it was in the target set. Several frontal areas—anterior cingulate (BA32), middle frontal gyrus (bilateral BA9, right BA10, and right BA46), and left inferior frontal gyrus (BA44/45)—showed increased activity when participants made correct negative responses relative to when they made correct positive responses.

Visual Imaging Using Techniques Other than FMRI

Blaizot et al. (2000) used PET data to map the visual recognition memory network in the baboon. Using computerized matching to sample visuomotor control tasks, they matched PET data to that obtained by anatomic MRI images. They found that foci of significant activation were distributed along the following brain areas: ventral occipitotemporal pathway, inferomedial temporal lobe, and orbitofrontal cortex, consistent with activation studies in healthy humans.

Additional Studies Indicating Location of Active Memory and Thought

In addition to the work of Ishai and of Zenich, referred to above, there are a number of other studies supporting the accessibility of neural data for interpretation of the actual thought processes occurring. Anderson et al. were able to record signals from neurons in monkeys and showed how they were coding for movement, an important step towards creating better prosthetic devices for paralyzed people. The decoded signals enabled the researchers to predict the monkeys' arm movements in tasks in which they thought about reaching for an item without actually doing so. Further, their research suggests that other types of cognitive signals can be decoded from patients.

Past studies on monkeys have shown that information from neurons coding movement instructions can be used to control prosthetic devices. For example, Rhesus monkeys could be taught to control and assimilate a robot arm using signals from their brain. To achieve this, researchers implanted an array of microelectrodes into the frontal and parietal lobes—areas of the brain involved in producing multiple output commands to control complex muscle movements. The faint brain signals from the electrodes were detected and analyzed by a computer system to recognize patterns of signals that represent particular movements by an animal's arm. These signals were translated into similar movements of a robotic arm.

Andersen and colleagues implanted in monkeys arrays of electrodes into areas of the brain that encode the goals of reaching movements rather than controlling movement itself. While the monkeys waited for a cue that told them to reach for an icon flashing on a screen, a computer program interpreted the brain signals recorded by the electrodes. Once the "neuronal code" was cracked, the researchers used the program to decipher the direction that the monkeys were planning to reach for during trials in which they thought about reaching but didn't actually do so. When monkeys remained still while having thoughts that were consistent with requested movements, they received a reward.

At first, the program had trouble matching the monkeys' intentions to the icon's position much more often than chance. As the monkeys practiced thinking about reaching, however, their neural signals became stronger, enabling the program to decode the correct direction more frequently. Eventually, the program could predict the intended direction of the monkeys' reach as much as 67% of the time. When the monkeys knew that accurately thinking about the requested movement would yield a preferred reward, the computer's ability to predict direction improved by as much as 21%. For instance, recording thoughts from speech areas could alleviate the use by those unable to speak (stroke, other neurologic diseases) of more cumbersome letter boards and time-consuming spelling programs, or recordings from emotion centers could provide an online indication of a patient's emotional state.

The overall significance of these studies is that changes in the brain occur during active memory, and these changes can be observed using existing neuroimaging technologies.

Thus, there exists a need to translate neurologic changes occurring upon sensory or physical stimulation into a decipherable code allowing one to effectively read neurologic activity of an individual.

SUMMARY OF THE INVENTION

A method of interpreting cognitive response to a stimulus is disclosed. The method includes collecting baseline neural activity data from a subject absent a stimulus. Neural activity data is collected while the subject is being stimulated through exposure to a stimulus. A unique three-dimensional cognitive engram is then plotted representative of cerebral regions of stimulated neural activity caused by the stimulus.

A novel graphical representation is plotted in three dimensions to indicate the brain region response unique to that stimulus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
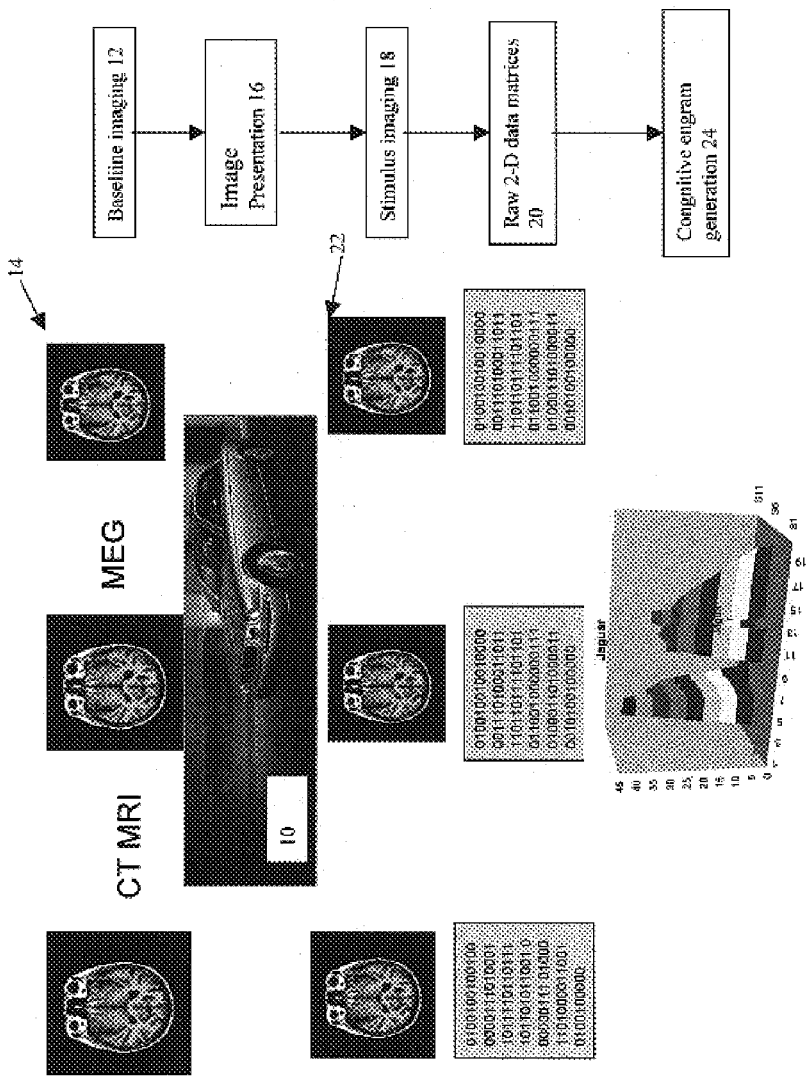
FIG. 1 is a schematic diagram of an inventive process to determine a cognitive engram.
Figure 2:
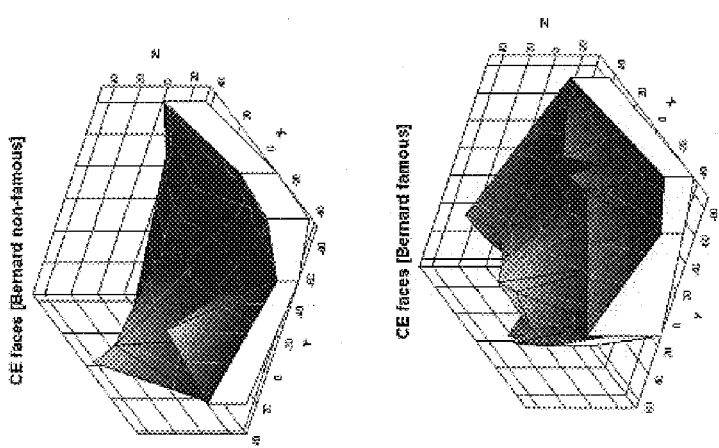
FIG. 2 is cognitive engrams derived from the data set of Bernard et al. (2003) for brain activity associated with anonymous and famous faces.

The present invention has utility in producing a cognitive engram representation of neuroimaging data associated with the neurophysiological changes that are responsible for storage of a specific memory element in the brain. The present invention finds utility in settings such as interrogation, national security, criminal investigation, marketing and pharmacology.

While a memory engram is known to one skilled in the art as a term that refers to the physical changes in the brain that accompany learning, as used herein the term "cognitive engram" is defined as a multidimensional representation of neuroimaging data of neurophysiological changes that are responsible for storage of a specific memory element or concept in the brain. A subset of a cognitive engram is appreciated herein to include truth/deception indications.

A "subject" is defined herein to include a human; non-human mammals such as monkeys, chimps, rats, mice, rabbits, dogs, cats, pigs, sheep and cows; and birds such as pigeons and chickens.

According to the present invention, cognitive engrams are described that capture memories of persons, places, events, concepts, intentions or thoughts from the brain of a subject and as such are readily adapted to discerning hidden agendas, past criminal activities, plans for the future, collaborative names, crime scene locations and other information that for instance is relevant to criminal investigations. It is appreciated that interrogation uses of the present invention are facilities by exposing a subject to stimulus while the subject is sedated, sleeping, or unconscious. Additionally, application of various stimuli to a given subject are applied directly onto the appropriate receptor organ (ear, eyes, etc.) or via direct brain stimulation To better illustrate the methods of the present invention for locating and uncoding cognitive data, the conceptual phrase "I took the car to the ATM and withdrew some cash" entails at least three images, namely an individual standing by an ATM machine, an image of a vehicle, and a cognitive image of currency. This conceptual phrase has numerous equivalent alternative phrases illustratively including "I took the car to the ATM, withdrew some cash"; "I got in the Jeep, took some money from the ATM"; "I got a ride to the bank for money"; and "Drove to ATM". If the exemplary conceptual phrase "I took the car to the ATM and withdrew some cash" were translated into a standard binary code, the resulting string of zeros and ones would not be readily understandable to a human. However, if every time a person's memory area is imaged while they are viewing an image of an ATM machine results in a string of values X, then this code represents a unique cognitive engram, in this case for an ATM machine. Additionally, according to the present invention it is not necessary to know how the representation is made so long as it is unique, repeatable and identifiable. As the brain represents a three-dimensional neuronal structure, the data necessary to derive a cognitive engram is not present in a single plane through the brain, but rather is found to be distributed through various portions of the brain and as such only a three-dimensional construction of a neural activation map is operative to display data indicative of, in the exemplary case, an ATM machine.

Referring now to FIG. 1, the schematic process for the determination of a cognitive engram is provided. In FIG. 1, the image 10 shown to a subject is that of a car and specifically a Jaguar brand vehicle. Before the subject is shown the image 10, a baseline MRI and functional MRI is taken of the test subject to provide baseline imaging 12 of the subject. Representative two-dimensional baseline scan images are shown at 14. The presentation of the image 10 in front of the subject 16 occurs while functional MRI test imaging 18 is collected. Representative two-dimensional MRI images are shown generally at 22 during image presentation 16. For each respective test slice 22, a compensation as detailed further below with respect to corresponding image 14 results in a series of two-dimensional numerical matrices representative of raw data 20. The raw data 20 is then combined and analyzed to provide a cognitive image engram 24 representative of the image 10. A representative engram for the car depicted in image 10 is shown at 26 and more specifically is unique not just for a car but for a Jaguar brand of vehicle.

Software for the analysis of raw imaging data 20 to identify unique cognitive engrams is surprisingly not critical with the proviso that like processing is used for subsequent experiments.

According to the present invention, manipulation of imaging data is as simple as subtracting a baseline image from each test scan from a subject brain. Alternatively, baseline two-dimensional MRI images and test two-dimensional view images are scanned for common patterns of data among groups of subjects exposed to the same or similar stimuli. In this way, a database of cognitive engrams can be developed common across populations in response to a particular stimulus. While the present invention has been detailed with respect to functional MRI data collection, it is appreciated that such data is optionally supplemented with CT, PET, MEG or EEG data. Such supplemental data is particularly helpful in constructing cognitive engrams representative of common responses to similar or identical stimulus. It is appreciated that conventional software routines are operative herein to construct spatially localized images and correlate concepts and items introduced via subject senses. Such software routines illustratively include subtracting test images 22 from corresponding baseline images 14, cryptography software, motion direction software that involves use of moving overlap, correlation across various imaging techniques, neural network software, statistical parametric mapping software, analysis of functional neuroimages (AFNI software), holographic routines and combinations thereof.

Gradient imaging is also optionally used to fluctuate the magnetic gradient of the MRI signal to enhance the resolution and content of the signal data. PET-MRI image registration is used to correlate images and data in both structural and functional terms. Although such data is obtained from separate scans with separate techniques, the resulting data extracted from the different scans on the same individual afford common structural and functional information. CT-MRI image fusion analysis is also operative herein to correlate images and data with both structural and functional components. This is analogous to PET-MRI image registration. In another embodiment, the comparison of dynamic MRI imaging with dynamic double arterial phase helical computer tomography is used to evaluate the structure and function of blood supply and perfusion and its relation to the encoding of memory. Virtual MRI constructions of finer resolution are appreciated to correlate functionally active regions of a subject brain to specific concept encoding. The resulting patterns are correlated through the stimulus a subject is being subjected to during neuroimaging. In other embodiment, three-dimensional image correlation of CT, magnetic resonance and PET studies are compared to further enhance structural and functional correlations within a subject brain and categorize those correlations with a stimulus or thought.

In still another embodiment, a functional magnetic resonance imaging in real-time (FIRE) uses sliding-window correlation analysis and reference-vector optimization of imaging data to understand encoding of specific stimulus as concepts within the subject brain in a mechanistic fashion.

In another embodiment, arterial spin labeling and dynamic susceptibility weighted contrast enhanced magnetic resonance imaging are used to discern, identify and match two-dimensional brain imaging data to the concepts being stored in a subject brain.

In another embodiment, comparison of conventional, magnetization transfer and diffusion-tensor magnetic resonance imaging findings is used with whole brain tissue histogram analysis to discern, identify and match two-dimensional brain imaging data to concepts being stored in a subject brain. Additionally, activation areas of a subject brain by groups of continuous voxels and by individual voxels are compared between individuals and within the same individual for multiple runs of the same stimulus. Additionally, windowing can be used to further simplify analysis such that instead of, for example, simply using maximal intensity by looking only at subject brain regions having for instance greater than 90% activity or only activity between 60% and 80%, a cognitive engram is more rapidly produced.

The net result of these varied image processing techniques that are applied in the generation and analysis of raw data is to discern a data storage pattern within the brain and prepare a Rosetta stone for the identification and matching of brain imaging scan data with a given stimulus without the need for understanding the rules of stimulus encoding within a subject brain.

Optionally, prior to determination of a cognitive engram, image corrections known to the art are performed to remove image noise. Such additional techniques illustratively include correcting for subject movement artifact, reprocessing sequential images, digital noise subtraction, blood oxygen level dependency consideration, statistical deformation modeling (SDM), and analysis algorithms well known to one skilled in the art for MRI data that exploits differences in data signals not requiring functional MRI or blood oxygen level dependent techniques.

An additional aspect of the present invention is the development of movement artifact overlap harvesting in which additional data removed by software to correct for movement artifact is harvested and processed to fill in detail from spatial areas between imaging slices and as such increases the total data set. The inventive technique of movement artifact overlap harvesting spatially plots conventional motion correction artifacts to create partial pseudoslices intermediate between adjacent MRI imaging slices.

The present invention is further detailed with respect to the following non-limiting examples.

EXAMPLE 1

Cognitive Engrams Extracted from Existing Studies

Recent scientific publications utilizing fMRI to study neurocognitive functions were located by searching the National Library of Medicine. Publications which detailed the specific coordinates of activation areas for visual objects were selected, and are described below. Three-dimensional graphical surface and bubble point representations of the activation maps were constructed by plotting the xyz coordinates. The xyz coordinates were supplied by all three sets of investigators using the normalized space of the Talairach and Tournoux brain atlas (1988).

All of the publications whose data was reprocessed presented test objects to test subjects while lying in an MRI scanner, using a flat panel display situated to allow visibility during scanning.

Bernard et al. (2004) studied the presentation and processing of visual imaging of famous and non-famous faces. The study used an event-related fMRI design, utilized a 4-T MRI system, with stimuli consisting of 80 black and white pictures of adult faces, half of famous and half of non-famous people. The xyz coordinates of the activation areas were supplied in Table 1 of the Bernard et al. publication. When the three-dimensional representation of Bernard et al. was prepared, the following cognitive engrams were determined.

When Bernard 2004 data was processed to create three-dimensional activation maps, two cognitive engrams were developed, one for famous and one for non-famous faces. It is apparent that by viewing these activation patterns, a determination of famous versus non-famous could be determined.

The data regenerated from Bernard et al. into cognitive engrams demonstrate the potential to distinguish whether specific faces are recognizable, and whether they are famous or non-famous. Differences between three classes of objects (face, chair, house), and familiar and non-familiar words can also be distinguished by the pattern of the cognitive engrams generated. With the development of more detailed activation maps, from a larger number of individuals, with a more detailed graphical representation of concepts, a Rosetta stone forming a database of cognitive engrams for individual faces, objects, places, and concepts (hate, intent to deceive, etc.) is being developed. Such a database allows the two-way interpretation of cognitive engrams, allowing the identification of the presence of specific thoughts (persons, places, intents) in an individual's brain.

EXAMPLE 2

Distinguishing Cognitive Engrams of Standard Faces

A 3-T General Electric Signa Excite scanner with whole head coil is used. Changes in the blood oxygen level dependent $T2^*$-weighted MRI signal are measured using a gradient-echo echoplanar sequence. In each time series, 18 (128× 128) or 28 (64×64) contiguous axial slices are obtained. There are three sets of scans performed per experiment: localizer, MRI for functional data, and high resolution anatomic.

The subject lies in the MRI scanner, wearing a phased array MRI head coil as part of the regular head scan. Mounted on the head coil is a 45 degree mirror, allowing them to see down toward their feet and view the test images. Displayed near the bottom of the subject's feet is a large photo, or a white blank paper board, which can have a large X marked across it, which is totally within the field of view of the test subject lying in the scanner. Other means of presentation of visual test images include a goggle image projection set, and use of an MRI-compatible video monitor.

The functional MRI scans last between 110 to 220 seconds total; after a 6 second lead-in time, the blank is displayed for 6 to 8 seconds, then the picture for 6 to 8 seconds, blank, picture, for a total of 5 to 10 repetitions.

In a separate scan, high-resolution full volume structural images are obtained for each subject, using fast SPGR imaging (146, 1.0-mm thick axial slices, no spaces, TR=8, TE=3.2, FOV=24 cm, 256×256 matrix). These T1-weighted images provided detailed anatomical information for registration and three-dimensional normalization to the Talairach and Tournoux atlas (1988), as described below.

There were about eight runs per person for these first few scans:

| Run | Process |
| --- | --- |
| 1 | Localizer (sets up scanner field, directs scanned areas into brain, avoids "ghost" images) |
| 2 | First photo |
| 3 | Second photo |
| 4 | Third photo (if used) |
| 5 | Detailed Anatomic run |

Data Analysis

Imaging data is analyzed in two ways: conventional and raw data. Conventional analysis refers to the generation of activation maps correlated with anatomical representative images. Modeling of raw imaging data involves the manipulation of the basic output from the scanner itself, using techniques such as neural networks. Voxels can be individually compared with the properties of intensity of activation and corrected spatial localization.

The following paragraphs explain the conventional analysis procedure. The FMRI scan volumes are motion-corrected and spatially smoothed in-plane. MRI data files are analyzed using MedX to determine the location of activated voxels—defined as voxels from a brain region that respond differentially to the test (visual) stimuli. Voxels are selected that show an overall increase in activity for meaningful stimuli, for example, a positive regression weight for the contrast between a test photo and control (blank page) stimuli. The uncorrected probability is >0.05, meaning every voxel showing activation with the probability of more than 95% is selected in the analysis.

Activated voxels are then segregated into clusters according to the category of objects that evoke the maximal response. For a conventional analysis, clusters of seven or more contiguous voxels are considered significant. In separate analyses, activated voxel data can also be parsed on the basis of degree of activation.

The anatomical locations of clusters of voxels showing significant differences between responses are determined by superimposing the statistical maps on coplanar high-resolution structural images. The partial volume structural images are registered with the full volume high-resolution images using Automated Image Registration (Woods, Mazziotta & Cherry, 1993).

The full volume high-resolution images are normalized to the Talairach and Tournoux atlas (1988) using MedX. Both transformations (registration and normalization) are then applied to the statistical maps, in order to obtain the Talairach coordinates of brain regions that respond maximally to the test stimuli to generate a cognitive engram.

Functional MRI experiments were performed on normal subjects, while they were looking at photos. As an example, the following activation map data points were created when viewing photos of President Bush and a grieving woman kneeling at grave site are detailed in Tables 1 and 2, respectively.

TABLE 1

Activation Points for President Bush

| | | | |
| --- | --- | --- | --- |
| Right Cerebrum, Limbic Lobe, Parahippocampal Gyrus, Gray Matter, Hippocampus | 32 | −20 | −14 |
| Left Cerebrum, Temporal Lobe, Inferior Temporal Gyrus, Gray Matter, Brodmann area 20 | −44 | −16 | −28 |
| Left Cerebrum, Temporal Lobe, Fusiform Gyrus, White Matter, * | −42 | −16 | −26 |
| Left Cerebrum, Temporal Lobe, Fusiform Gyrus, White Matter, * | −45 | −16 | −26 |
| Left Cerebrum, Temporal Lobe, Inferior Temporal Gyrus, White Matter, * | −44 | −18 | −28 |
| Left Cerebrum, Temporal Lobe, Inferior Temporal Gyrus, White Matter, * | −44 | −18 | −30 |
| Left Cerebrum, Temporal Lobe, Inferior Temporal Gyrus, White Matter, * | −45 | −18 | −28 |

TABLE 2

Activation Points for Grieving Female

| Location | X | Y | Z |
| --- | --- | --- | --- |
| Left Cerebrum, Temporal Lobe, Sub-Gyral, White Matter, * | −40 | −11 | −14 |
| Left Cerebrum, Temporal Lobe, Sub-Gyral, White Matter, * | −38 | −9 | −14 |
| Left Cerebrum, Temporal Lobe, Sub-Gyral, White Matter, * | −38 | −10 | −14 |
| Left Cerebrum, Temporal Lobe, Sub-Gyral, White Matter, * | −36 | −8 | −14 |
| Left Cerebrum, Temporal Lobe, Sub-Gyral, White Matter, * | −38 | −7 | −16 |
| Left Cerebrum, Temporal Lobe, Sub-Gyral, White Matter, * | −38 | −6 | −14 |
| Left Cerebrum, Limbic Lobe, Parahippocampal Gyrus, Gray Matter, Brodmann area 36 | −25 | −36 | −14 |
| Left Cerebrum, Limbic Lobe, Parahippocampal Gyrus, Gray Matter, Brodmann area 36 | −24 | −33 | −14 |
| Left Cerebrum, Temporal Lobe, Fusiform Gyrus, *, * | −26 | −38 | −14 |
| Left Cerebrum, Temporal Lobe, Fusiform Gyrus, Gray Matter, Brodmann area 37 | −27 | −41 | −14 |
| Left Cerebrum, Temporal Lobe, Fusiform Gyrus, *, * | −26 | −38 | −14 |
| Left Cerebrum, Limbic Lobe, *, *, * | −23 | −38 | −12 |
| Left Cerebrum, Temporal Lobe, Fusiform Gyrus, *, * | −25 | −40 | −12 |
| Left Cerebrum, Temporal Lobe, *, *, * | −29 | −40 | −16 |
| Left Cerebrum, Temporal Lobe, Fusiform Gyrus, *, * | −28 | −34 | −16 |
| Left Cerebrum, Temporal Lobe, Fusiform Gyrus, Gray Matter, Brodmann area 37 | −28 | −38 | −14 |

Figure 3:
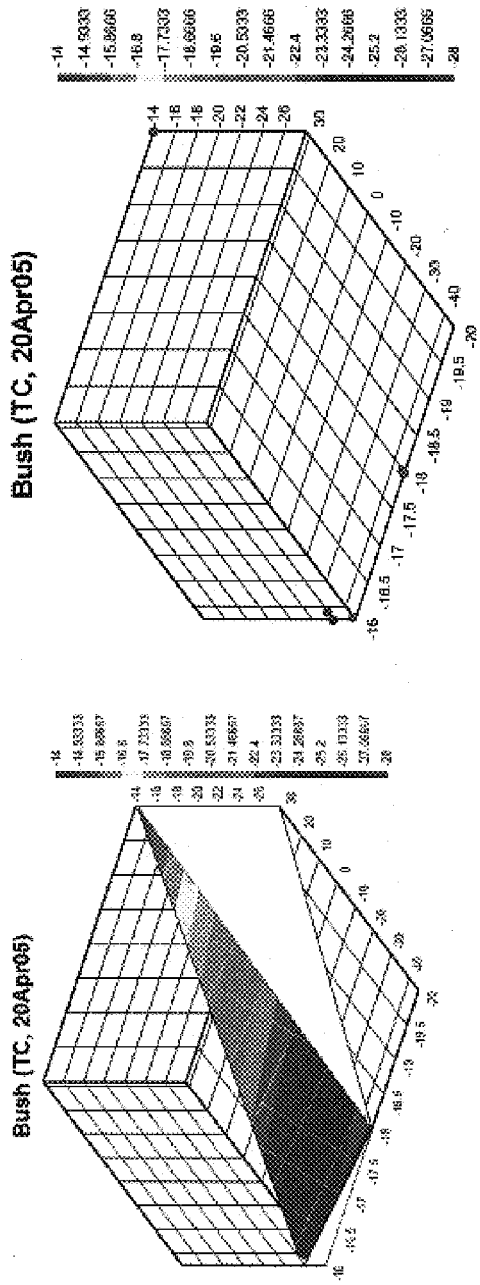
FIG. 3 is a cognitive engram from a subject viewing an image of President Bush.
Figure 4:
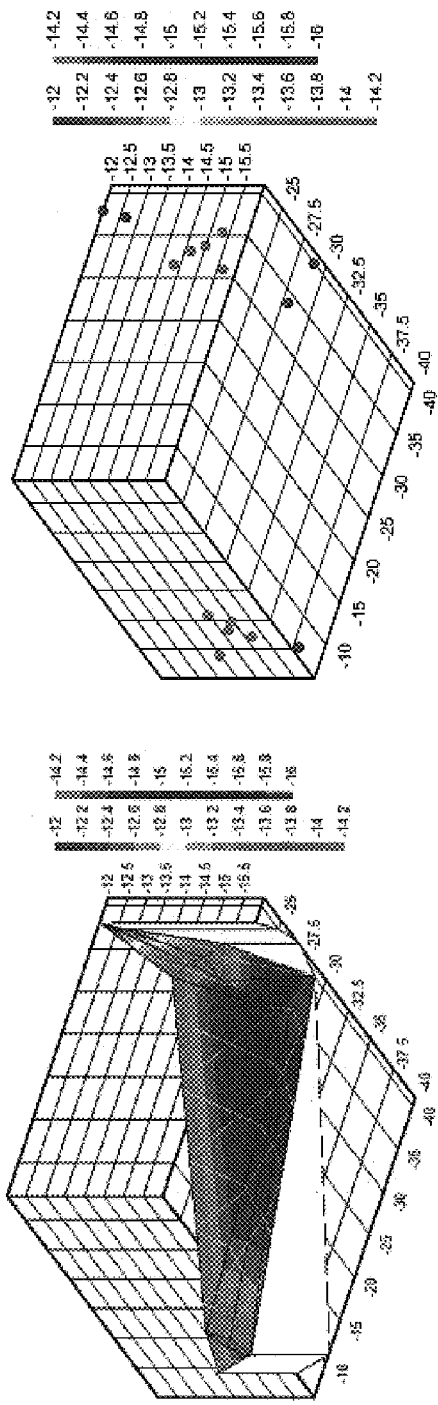
FIG. 4 is a cognitive engram from a subject viewing a grieving woman by a grave.
Figure 5:
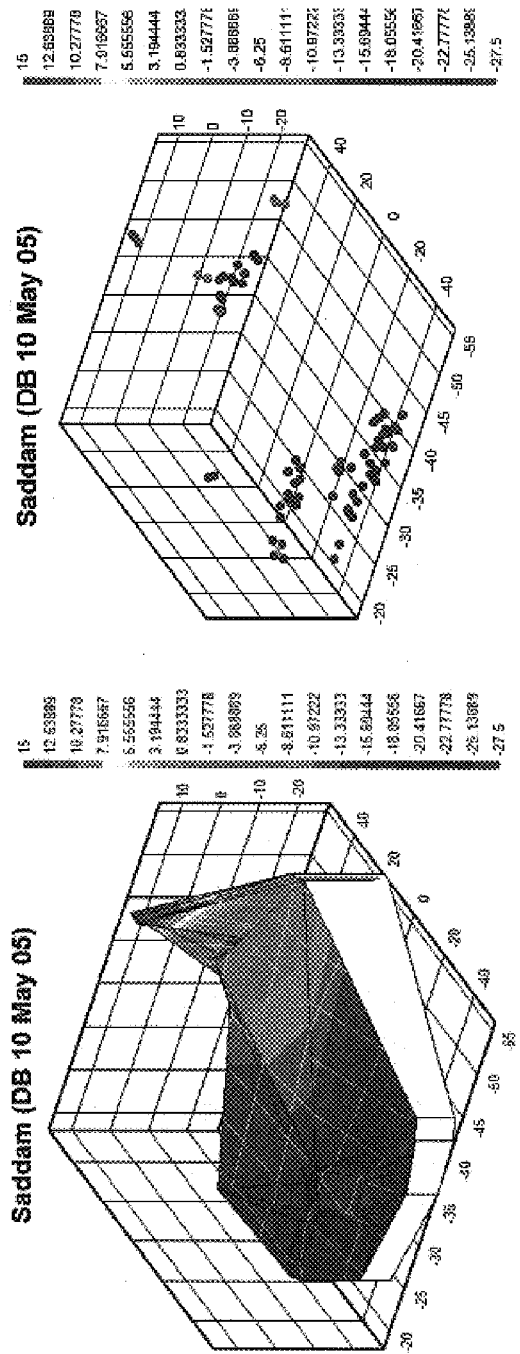
FIG. 5 is a cognitive engram from a subject viewing an image of Saddam Hussein.
Figure 6:
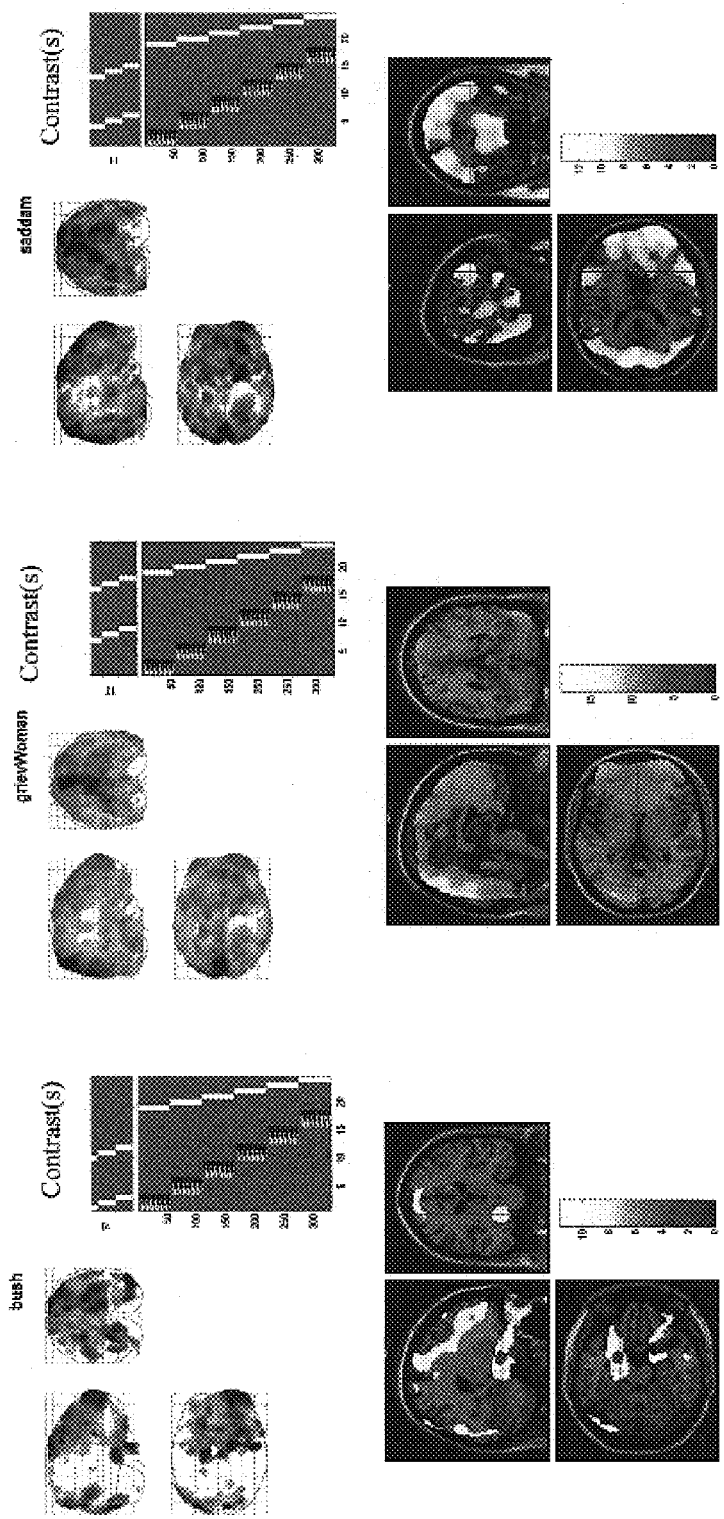
FIG. 6 is function magnetic resonance images collected from the same individual, viewing the images of FIGS. 3-5, indicating similar areas of general visual activation, and also areas indicate specific differentiating areas.

Cognitive engrams derived from scans of a subject brain while viewing photos of President Bush, a grieving woman kneeling at a graveside, and Saddam Hussein are shown in FIGS. 3, 4, and 5, respectively. The fMRIs from the same individual, viewing these images are shown in FIG. 6, where similar areas of general visual activation arte noted, and also areas that are indicative of specific differentiating areas. By using an activation map composed of xyz coordinates and intensity windows, such as areas with greater than 90% activity, 60 to 80% activity, etc. a fourth dimension of activity intensity topography is overlapped onto an inventive cognitive engram.

EXAMPLE 3

Sample Interrogation Protocol

Background information is obtained on the subject's name, age, sex, SSN, birth city, medications, current and past illnesses, psych history, criminal history, accusation. Then, a basic set of standard images is presented to the test subject while undergoing neuroimaging, in order to obtain a background pattern of activation. Individual responses to questions are recorded via a number of techniques, including verbal and pressing of buttons on handgrips. The test subject is presented with between ten to twenty test questions, and asked to supply intentionally deceptive and intentionally truthful responses to each question.

The test subject is presented with case-specific questions, with accompanying images/displays of words and phrases concerning:

Facts about their own personal life, name, sex, age, SSN, residence, criminal history; and Specific photos/questions/statements relating to the subject at issue, including potentially the specific crime, intention, conspiracy collaborators, locations, objects.

The raw imaging data (structure and function) is analyzed and three-dimensional activation and anatomical maps are created. The pattern of activation is correlated with specific responses to images and concepts, as part of a correlative dictionary (Rosetta stone) between three-dimensional FMRI activation maps and concepts/images presented.

The activation map is analyzed according to Example 2 to create the optimum correlation between activation areas and truthful/deceptive responses on control and question images/concepts. Using the internal controls on individual patients, and accumulated group controls, an interpretation on truthfulness is made for:

responses to individual questions; and recognition of individual presented images and concepts.

EXAMPLE 4

Use of fMRI to Predict Neurologic Adverse Effects of Interferon Used to Treat Patients with Hepatitis C Brain activation cognitive engrams of individuals who have been selected to receive interferon therapy are produced, before and after 4-6 weekly injections of interferon. Standard medical questioning and written evaluation tools of depression such as Beck Depression Scale are employed at baseline and weekly to detect the development of INF-associated depression. Individuals who require treatment of interferon-induced depression (receive an antidepressant such as SSRI medication) undergo repeat fMRI after an appropriate therapeutic interval, in order to evaluate changes in activation map which can correlate with a therapeutic antidepressive response.

Immediate follow-up studies include dose-response of interferon to fMRI indices of clinical depression, and response of depression, as shown by fMRI indices of depression, to antidepressant drugs. The immediate benefit of this is to develop an objective method of predicting a depressive response to depressant side effects of essential medications. The response predictive protocol is provided in Table 3.

TABLE 3

Interferon Study Design

| | | | |
|---|---|---|---|
| 1 | Pre-Protocol | Eligibility Screening | |
| 2 | Eligible patient | MRI and fMRI | Beck Depression Scale |
| 3 | Week 1 | Begin hepatitis C treatment, including interferon | |
| 4 | Week 4-6, or sooner if significant adverse CNS symptoms develop | MRI and fMRI | Beck Depression Scale |
| 5 | If CNS symptoms, but are not severe enough to discontinue interferon, begin an antidepressant | | |
| 6 | 2-4 weeks antidepressant | MRI and fMRI | Beck Depression Scale |

The study subjects undergo continual MRI neuroimaging while viewing test stimuli in order to capture structural and functional data as detailed in Example 2. These data are analyzed for the presence of neuroimaging activation that has been shown to correspond to cognition and depression.

Test visual stimuli are chosen to induce a strong depressive response in the viewer.

A normal test subject was shown photos of President Bush, Saddam Hussein, and of a grieving woman kneeling at a grave as detailed in Example 2. The photo of the grieving woman was used to generate a feeling of sadness. This person showed activation in the right inferior and middle temporal gyrus, and in the fusiform gyrus, areas known to correlate with the provocation of sadness in normal individuals. This activation was only noted when viewing the grieving woman, not for the test photos of President Bush and Saddam Hussein. Individuals scoring as depressed on the Beck Depression Scale showed varying degrees of activation in these cerebral regions for all three images.

REFERENCES

Beauchamp M H et al. Dynamic functional changes associated with cognitive skill learning of an adapted version of the Tower of London task. Neuroimage. 2003 November; 20(3):1649-60.

Bernard F A et al. The hippocampal region is involved in successful recognition of both remote and recent famous faces. NeuroImage 22 (2004) 1704-1714.

Binder J R et al. Conceptual Processing During the Conscious Resting State: A functional MRI Study. J Cog Neuroscience 11(1):80-93, 1999.

Binder J R et al. Neural Correlates of Lexical Access during Visual Word Recognition. Journal of Cognitive Neuroscience 15:3, pp. 372-393, 2003.

Blair, R J R et al. Dissociable neural responses to facial expressions of sadness and anger. Brain (1999), 122, 883-893.

Blaizot X. et al. Mapping the visual recognition memory network with PET in the behaving baboon. J Cereb Blood Flow Metab. 2000 February; 20(2):213-9.

Bloom A S et al. Determination of Drug-Induced Changes in Functional MRI Signal Using a Pharmacokinetic Model. Hum Brain Mapping 8:235-244, 1999.

Buhmann C et al. Pharmacologically modulated fMRI-cortical responsiveness to levodopa in drug-naïve hemiparkinsonian patients. Brain 126, 451-461, 2003.

Canli T et al. Brain activation to emotional words in depressed vs healthy subjects. Brainimaging Neuroreport. Vol 15, No 17, 3 Dec. 2004 2585.

Chao L L, Haxby J V, Martin A. Attribute-based neural substrates in temporal cortex for perceiving and knowing about objects. Nat Neurosci. 1999 October; 2(10):913-9.

Chua P et al. A functional anatomy of anticipatory anxiety. NeuroImage 9: 563-571, 1999.

Courthey S M, Petit L, Haxby J V, et al. The role of prefrontal cortex in working memory: examining the contents of consciousness. Philos Trans R Soc Lond B Biol Sci. 1998 Nov. 29; 353(1377):1819-28.

Critchley H D, Elliott R, Mathias C J, Dolan R J. Neural activity relating to generation and representation of galvanic skin conductance responses: A functional magnetic resonance imaging study. J. Neurosci. 20: 3033-3040, 2000.

Dougherty D D, Rauch S L, Jenike M A. (2004). Pharmacotherapy for Obsessive-Compulsive Disorder. JCLP/In Session 60, 1195-1202.

Dodson C S, Johnson M K. Rate of false source attributions depends on how questions are asked. Am J Psychol. 1993 Winter; 106(4):541-57.

Fossati P, Radtchenko A, Boyer P. (2004). Neuroplasticity: from MRI to depressive symptoms. European Neuropsychopharmacology 14, S503-S510.

Fan J et al. Functional magnetic resonance imaging of source versus item memory. Neuroreport. 2003 Dec. 2; 14(17): 2275-81.

Fiebach C J, Friederici A D. Processing concrete words: FMRI evidence against a specific right-hemisphere involvement. Neuropsychologia. 2004; 42(1):62-70.

Fletcher P C, Henson R N. Frontal lobes and human memory: insights from functional neuroimaging. Brain (2001 May) 124(Pt 5):849-81. pcf22@cam.ac.uk.

Fossati P et al. Neuroplasticity: from MRI to depressive symptoms. European Neuropsychopharmacology 14 (2004) S 503-S 510.

Fossati P et al. In search of the emotional self: an FMRI study using positive and negative emotional words. Am J Psychiatry. 2003 November; 160(11):1938-45. philippe.fossatiΩpsl.ap-hop-paris.fr.

Fu C H et al. Attenuation of the neural response to sad faces in major depression by antidepressant treatment: a prospective, event-related functional magnetic resonance imaging study. Arch Gen Psychiatry. 2004 September; 61(9):877-89.

Fujii T et al. Encoding-related brain activity during deep processing of verbal materials: a PET study. Neurosci Res Vol. 44 2002 December pp. 429-38.

Gaillard W D, Hertz-Pannier L, Mott S H, Barnett A S, LeBihan D, Theodore W H. Functional anatomy of cognitive development: FMRI of verbal fluency in children and adults. Neurology (2000 Jan. 11) 54(1):180-5 gaillardw@ninds.nih.gov.

Gerlach C et al. Perceptual differentiation and category effects in normal object recognition: a PET study. Brain (1999 November) 122 (Pt 11):2159-70 cgerlach@axp.psl.ku.dk.

Gevins A et al. Electroencephalographic imaging of higher brain function. Philos Trans R Soc Lond B Biol Sci. 1999 Jul. 29; 354(1387):1125-33.

Gonsalves B et al. Neural evidence that vivid imagining can lead to false remembering. Psychological Science 15(10): 655-660, 2004.

Gross J et al. Properties of MEG tomographic maps obtained with spatial filtering. Neuroimage. 2003 August; 19(4): 1329-36.

Gur R C, Gur R E, Resnick S M, Skolnick B E, Alavi A, Reivich M. The effect of anxiety on cortical cerebral blood flow and metabolism. J. Cereb. Blood Flow Metab. 7: 173-177, 1987.

Hagoort P. How the brain solves the binding problem for language: a neurocomputational model of syntactic processing. Neuroimage. 2003 November; 20 Suppl 1:S18-29. peter.hagoort@fcdonders.kun.nl.

Hammers A et al. Three-dimensional maximum probability atlas of the human brain, with particular reference to the temporal lobe. Hum Brain Mapp. 2003 August; 19(4):224-47.

Hartley A A, Speer N K. Locating and fractionating working memory using functional neuroimaging: storage, maintenance, and executive functions. Microsc Res Tech. 2000 Oct. 1; 51(1):45-53.

Haxby J V, Gobbini M I, Furey M L et al. Distributed and Overlapping Representations of Faces and Objects in Ventral Temporal Cortex. Science Vol 293 28 Sep. 2001 2425.

Haxby J V et al. Object-form topology in the ventral temporal lobe. Response to I. Gauthier (2000). Trends Cogn Sci. 2000 January; 4(1):3-4.

Henson R N. Neuroimaging studies of priming. Prog Neurobiol. 2003 May; 70(1):53-81.

Ishai A et al. Distributed representation of objects in the human ventral visual pathway. 1999 PNAS. 96:9379-9384.

Ishai A et al. The representation of objects in the human occipital and temporal cortex. (2000) Journal of Cognitive Neuroscience, 12 Supplement 2, pp. 35-51.

Jernigan T L et al. More "mapping" in brain mapping: statistical comparison of effects. Hum Brain Mapp. 2003 June; 19(2):90-5.

Johnson M K, Hashtroudi S, Lindsay D S. Source monitoring. Psychological Bulletin 114:3-28, 1993.

Juengling, F D et al. Prefrontal cortical hypometabolism during low-dose interferon alpha treatment. Psychopharmacology 152, 383-389, 2000.

Kim D S, Kim M, Ronen I et al. In vivo mapping of functional domains and axonal connectivity in cat visual cortex using magnetic resonance imaging. Magn Reson Imaging. 2003 December; 21(10):1131-40.

Knight D C et al. Neural substrates mediating human delay and trace fear conditioning. J. Neurosci. 2004 Jan. 7; 24(1): 218-28.

Koechlin E, Ody C, Kouneiher F. The architecture of cognitive control in the human prefrontal cortex. Science. 2003 Nov. 14; 302(5648):1181-5. Comment in: Science. 2003 Nov. 14; 302(5648):1133 PMID: 14615503.

Koechlin E et al. The architecture of cognitive control in the human prefrontal cortex. Science. 2003 Nov. 14; 302(5648):1181-5.

Kozel A, Padgett T M, George M S. A Replication Study of the Neural Correlates of Deception. Behavioral Neuroscience, Vol. 118, No. 4, 2004.

Lange N. What can modern statistics offer imaging neuroscience? Stat Methods Med Res. 2003 October; 12(5):447-69. nlange@hms.harvard.edu.

Langleben D D et al. Brain Activity during Simulated Deception: An Event-Related Functional Magnetic Resonance Study. NeuroImage 15, 727-732 (2002).

Lee T M et al. Lie Detection by Functional Magnetic Resonance Imaging. Hum. Brain Mapping 15:157-164, 2002.

Lykken, D T. 1991. Why (some) Americans believe in the lie detector while others believe in the guilty knowledge test. Integr. Physiol. Behav. Sci. 26: 214-222.

Matthews, S C, Paulus, M P, Dimsdale, J E. (2004). Contribution of functional neuroimaging to understanding neuropsychiatric side effects of interferon in Hepatitis C. Psychosomatics 45, 281-286.

McGonigle D J et al. Variability in fMRI: An examination of intersession differences. NeuroImage, 11, 708-734, 2000.

Lanius R A et al. The nature of traumatic memories: a 4-T FMRI functional connectivity analysis. Am J Psychiatry. 2004 January; 161(1):36-44.

Lanius R A, Williamson P C, Densmore M et al. The nature of traumatic memories: a 4-T FMRI functional connectivity analysis. Am J Psychiatry. 2004 January; 161(1):36-44.

Marshall J C, Fink G R. Cerebral localization, then and now. Neuroimage. 2003 November; 20 Suppl 1:S2-7. john.marshall@clneuro.ox.ac.uk.

Maldjian J A et al. An automated method for neuroanatomic and cytoarchitectonic atlas-based interrogation of FMRI data sets. Neuroimage. 2003 July; 19(3): 1233-9.

McGonigle D J et al. Variability in fMRI: An examination of intersession differences. NeuroImage, 11, 708-734, 2000.

Michael D et al. The neural basis of episodic memory: evidence from functional neuroimaging. Phil. Trans. R. Soc. Lond. B (2002) 357, 1097-1110 1097.

Mungas D et al. MRI predictors of cognition in subcortical ischemic vascular disease and Alzheimer's disease. Neurology (2001 Dec. 26) 57(12):2229-35 dmmungas@ucdavis.edu.

Na, D G et al. Functional MR imaging of working memory in the human brain. Korean J Radiol 2000 January-March pp. 19-24.

Nielsen F A et al. Mining for associations between text and brain activation in a functional neuroimaging database. Neuroinformatics. 2004; 2(4):369-80.

Nyberg L et al. Brain imaging of human memory systems: between-systems similarities and within-system differences. Brain Res Cogn Brain Res, Vol. 13, 2002 April, pp. 281-92.

National Research Council. (2003). *The polygraph and lie detection*. Retrieved December, 2004, from the National Academies Web site: http://www.nap.edu/books/0309084369/html/.

Ogawa S, Lee T M, Kay A R, Tank D W. Brain magnetic resonance imaging with contrast dependent on blood oxygenation. Proc Natl Acad Sci USA. 1990 December; 87(24):9868-72.

Okado Y and Stark C, J H U. Neural processing associated with true and false memory retrieval. Cognitive, Affective, & Behavioral Neuroscience. 2003, 3 (4), 323-334.

Olesen P J et al. Increased prefrontal and parietal activity after training of working memory. Nat Neurosci. 2004 January; 7(1):75-9.

Papadakis N G et al. A measure of curve fitting error for noise filtering diffusion tensor MRI data. J Magn Reson. 2003 September; 164(1):1-9.

Pietrini P, Furey M L, Ricciardi E, et al. Beyond sensory images: Object-based representation in the human ventral pathway. Proc Natl Acad Sci USA. 2004 Apr. 13; 101(15): 5658-63. Epub 2004 Apr. 2.

Prabhakaran V, Narayanan K, Zhao Z et al. Integration of diverse information in working memory within the frontal lobe. Nat Neurosci. 2000 January; 3(1):85-90.

Reber P J et al. Neural correlates of successful encoding identified using functional magnetic resonance imaging. J. Neuroscience. 22:9541-9548, 2002.

Robertson L T. Memory and the brain. J Dent Educ. 2002 January; 66(1):30-42.

Rugg M D, Otten L J, Henson R N. The neural basis of episodic memory: evidence from functional neuroimaging. Phil. Trans. R. Soc. Lond. B (2002) 357, 1097-1110.

Rueckert D, Frangi A F, Schnabel J A. Automatic construction of 3-D statistical deformation models of the brain using nonrigid registration. IEEE Trans Med Imaging. 2003 August; 22(8):1014-25.

Salmeron B J, Stein E A. Pharmacological applications of magnetic resonance imaging. Psychopharmacol Bull (2002 Winter) 36(1):102-29.

Schmithorst V J, Holland S K. Comparison of three methods for generating group statistical inferences from independent component analysis of functional magnetic resonance imaging data. J Magn Reson Imaging. 2004 March; 19(3): 365-8.

Szaflarski J P, Holland S K et al. High-resolution functional MRI at 3T in healthy and epilepsy subjects: hippocampal activation with picture encoding task. Epilepsy Behav. 2004 April; 5(2):244-52.

Schmithorst V J et al. Cognitive functions correlate with white matter architecture in a normal pediatric population: A diffusion tensor MRI study. Hum Brain Mapp. 2005 Apr. 27.

Slotnick S D and Schacter D L. A sensory signal that distinguishes true from false memories. Nature Neuroscience 7(6):664-669, 2004.

Shallice T. Functional imaging and neuropsychology findings: how can they be linked? Neuroimage. 2003 November; 20 Suppl 1:S146-54. t.shallice@ucl.ac.uk.

Smejkal V, Druga R, Tintera J. Olfactory activity in the human brain identified by FMRI. Bratisl Lek Listy. 2003; 104(6): 184-8.

Smith C D, Andersen A H, Kryscio R J et al. Altered brain activation in cognitively intact individuals at high risk for Alzheimer's disease. Neurology (1999 Oct. 22) 53(7): 1391-6.

Sobottka S B et al. Comparison of functional brain PET images and intraoperative brain-mapping data using image-guided surgery. Comput Aided Surg. 2002; 7(6): 317-25.

Stuss D T, Gallup G G, Alexander M P. The frontal lobes are necessary for "theory of mind". Brain (2001 February) 124(Pt 2):279-86. dstuss@rotman-baycrest.on.ca.

Suppes P and Han B. Brain-wave representation of words by superposition of a few sine waves. Proc Natl Acad Sci USA. 2000 Jul. 18; 97(15): 8738-8743.

Talairach J and Toumoux P. (1988). *Co-planar stereotaxis atlas of the human brain* (M. Rayport, Trans.). New York: Thieme Medical.

Thomas K M. Assessing brain development using neurophysiologic and behavioral measures. J Pediatr. 2003 October; 143(4 Suppl):S46-53.

Vythilingam M et al. Hippocampal Volume, Memory, and Cortisol Status in Major Depressive Disorder: Effects of Treatment. Biol. Psychiatry 56, 101-112, 2004.

Wood E R, Dudchenko P A, Robitsek R J, Eichenbaum H. Hippocampal neurons encode information about different types of memory episodes occurring in the same location. Neuron (2000 September) 27(3):623-33.

Wagner A D, Koutstaal W, Schacter D L. When encoding yields remembering: Insights from event-related neuroimaging. Philas. Transact. Royal Soc London. B. Biological Sciences. 354:1307-1324, 1999.

Woods R P, Mazziotta J C, Cherry S R. MRI-PET registration with automated algorithm. J Comput Assist Tomogr. 1993 July-August; 17(4):536-46.

Wyland C L, Kelley W M, Macrae C N, Gordon H L, Heatherton T F. Neural correlates of thought suppression. Neuropsychologia. 2003; 41(14):1863-7.

Yin, J C. Location, location, location: The many addresses of memory formation. Proc. Natl. Acad. Sci. USA Vol. 96, pp. 9985-9986, August 1999.

Yang Y, Gu H, Stein E A (2004). Simultaneous MRI Acquisition of Blood Volume, Blood Flow, and Blood Oxygenation Information during Brain Activation. Magnetic Res. Medicine 52, 1407-1417.

Zhang J X, Leung H C, Johnson M K. Frontal activations associated with accessing and evaluating information in working memory: an FMRI study. Neuroimage. 2003 November; 20(3):1531-9.

Zeineh M M, Engel S A, Thompson P M, et al. Dynamics of the hippocampus during encoding and retrieval of face-name pairs. Science 299, 24 Jan. 3, pp 577-580.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method of interpreting cognitive response comprising:
   collecting baseline neural activity data that maps a neural activation absent a stimulus onto neuronal structure of a subject brain of a plurality of subjects absent said stimulus;
   exposing each of said plurality of subjects to said stimulus;
   collecting stimulated neural activity data that maps a neural activation during said stimulus onto said neuronal structure of the subject brain from each of said plurality of subjects while each of said plurality of subjects is exposed to said stimulus;
   plotting a unique three-dimensional cognitive engram representative of a common stimulated neural activity caused by said stimulus from said plurality of subjects to a level of voxels; and
   compiling said cognitive engram in a database containing a plurality of engrams, each of said plurality of engrams associated with a different stimulus for interpreting cognitive response.

2. The method of claim 1 wherein said stimulus is sensory.

3. The method of claim 1 wherein said stimulus is viewing an image.

4. The method of claim 1 wherein said stimulus is a verbal question of recall.

5. The method of claim 1 wherein said stimulus is chemical.

6. The method of claim 1 wherein said stimulus is drug administration.

7. The method of claim 6 further comprising correlating said cognitive engram with a regimen of said drug administration.

8. The method of claim 1 wherein said subject is a human.

9. The method of claim 1 wherein said baseline data and said stimulated data are collected with a technique selected from the group consisting of: magnetic resonance imaging, functional magnetic resonance imaging, computerized tomography, positron emission tomography, electroencephalogram, magnetic encephalogram, and combinations thereof.

10. The method of claim 1 wherein said baseline data and said stimulated data for one of said plurality of subjects are collected as a plurality of tomographic scans compiled as two-dimensional slices.

11. The method of claim 1 further comprising performing image noise removal from said stimulated data for one of said plurality of subjects prior to plotting said cognitive engram.

12. The method of claim 1 further comprising performing an operation on said stimulated data prior to plotting said cognitive engram, said operation selected from the group consisting of: correcting for subject movement artifact, reprocessing sequential images, blood oxygen level dependency consideration and statistical deformation modeling.

13. The method of claim 1 further comprising harvesting subject movement artifact overlap data for one of said plurality of subjects for said stimulated data prior to plotting said cognitive engram.

14. The method of claim 1 wherein said baseline data and said stimulated data for one of said plurality of subjects are derived from functional magnetic resonance imaging.

15. The method of claim 14 wherein said functional magnetic resonance imaging is correlated with data obtained from a technique selected from the group consisting of: positron emission tomography and computerized tomography.

16. The method of claim 1 wherein said baseline data and said stimulated data for one of said plurality of subjects are derived from arterial spin labeling and dynamic susceptibility weighted contrast enhanced magnetic resonance imaging.

17. The method of claim 1 wherein said baseline and said stimulated data for one of said plurality of subjects are derived from magnetization transfer and diffusion-tensor magnetic resonance imaging with whole brain tissue histogram analysis.

18. The method of claim 1 further comprising:
   comparing a test subject neural activity data that maps test subject neural activation onto test subject neuronal brain structure with said plurality of engrams in said database.

19. A method of questioning a subject comprising:
   (a) exposing a plurality of control subjects to a known truthful question;
   (b) collecting stimulated neural activity data that maps known truthful neural activation during exposure to the known truthful question onto neuronal structure of a subject brain from each of said plurality of control subjects;
   (c) plotting a unique truthful question three-dimensional cognitive engram representative of a common truthful neural activity associated with the known truthful question from said plurality of subjects to a level of voxels;
   (d) exposing said plurality of control subjects to a known falsehood;
   (d') collecting stimulated neural activity data that maps known truthful neural activation during exposure to the known falsehood onto neuronal structure of a subject brain from each of said plurality of control subjects;

(e) plotting a unique known falsehood three-dimensional cognitive engram representative of a common falsehood neural activity of the known falsehood from said plurality of subjects to a level of voxels;

(g) exposing said subject to a question of unknown truthfulness;

(h) collecting stimulated neural activity data that maps the question of unknown truthfulness neural activation from said subject during exposure to the question of unknown truthfulness; and (i) comparing said unique unknown data that maps the question of unknown truthfulness neural activation as being more closely aligned with one of said truthful question three-dimensional cognitive engram or said known falsehood three-dimensional cognitive engram.

20. The method of claim 19 further comprising repeating steps (a)-(i) with said subject in a different state, the state is selected from the group consisting of: physiology, psychological disease state, response to a chemical stimulus, and a level of pain.

21. The method of claim 20 wherein the subject's state is response to a chemical stimulus, wherein said chemical stimulus is induced by administration of a drug selected from the group consisting of: interferon, quinolones, neuroleptics, serotonin-active drugs, and alcohol.

* * * * *

UNITED STATES PATENT AND TRADEMARK OFFICE
CERTIFICATE OF CORRECTION

PATENT NO. : 7,627,370 B2  Page 1 of 1
APPLICATION NO. : 11/180871
DATED : December 1, 2009
INVENTOR(S) : Donald H. Marks It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this

Second Day of November, 2010

David J. Kappos
*Director of the United States Patent and Trademark Office*